United States Patent [19]

Cole et al.

[11] 4,249,081
[45] Feb. 3, 1981

[54] DEFECT DETECTION SYSTEM

[75] Inventors: Frederick A. Cole; Ronald L. Deak, both of Jackson, Mich.

[73] Assignee: Sparton Corporation, Jackson, Mich.

[21] Appl. No.: 90,335

[22] Filed: Nov. 1, 1979

[51] Int. Cl.³ ............................................. G01N 21/88
[52] U.S. Cl. ..................................... 250/563; 250/572
[58] Field of Search ............... 250/559, 562, 563, 572, 250/214 R; 356/445, 448, 238, 429, 430, 431

[56] References Cited

U.S. PATENT DOCUMENTS

| | | |
|---|---|---|
| 3,160,759 | 12/1964 | Ward . |
| 3,206,606 | 9/1965 | Burgo et al. . |
| 3,325,649 | 6/1967 | Bird . |
| 3,551,678 | 12/1970 | Mitchell . |
| 3,589,816 | 6/1971 | Sugaya . |
| 3,729,635 | 4/1973 | Shottenfeld et al. ................. 250/562 |
| 3,736,428 | 5/1973 | Monroe . |
| 3,786,265 | 1/1974 | Abilock et al. . |
| 3,812,373 | 5/1974 | Hosoe et al. ......................... 250/562 |
| 3,850,526 | 3/1973 | Corey . |
| 3,859,538 | 1/1975 | Mannonen ........................... 356/430 |
| 3,994,586 | 11/1976 | Sharkins et al. . |
| 4,011,457 | 3/1977 | Wolf .................................... 250/563 |
| 4,057,351 | 11/1977 | Fomenko . |
| 4,075,498 | 2/1978 | Takasuka et al. . |
| 4,103,177 | 7/1978 | Sanford et al. ...................... 250/562 |
| 4,110,048 | 8/1978 | Akutsu et al. ....................... 250/563 |
| 4,134,684 | 1/1979 | Jette .................................... 250/563 |

*Primary Examiner*—David C. Nelms
*Attorney, Agent, or Firm*—Beaman & Beaman

[57] ABSTRACT

The invention pertains to a defect detection system for inspecting fabric wherein fabric is scanned by electronic light-sensing apparatus for inconsistencies in light reflecting capability and defects produce electronic signals which are counted, and preferably, are automatically counted with respect to a predetermined time interval wherein fabric manufacturing apparatus may be automatically monitored to maintain a predetermined quality of product. Preferably, infrared frequencies are utilized for defect sensing purposes and electronic signal retention counting and timing apparatus automatically terminates fabric production if defect occurence exceeds a predetermined frequency in a given time interval.

7 Claims, 9 Drawing Figures

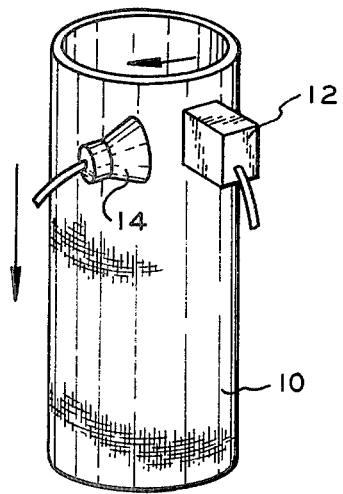
FIG._1.
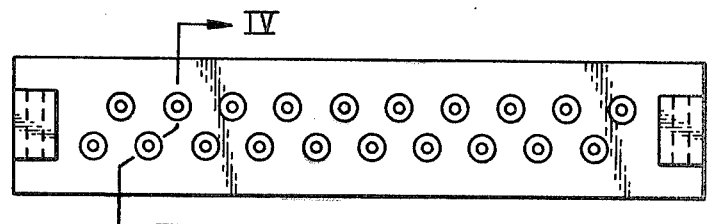
FIG._2.
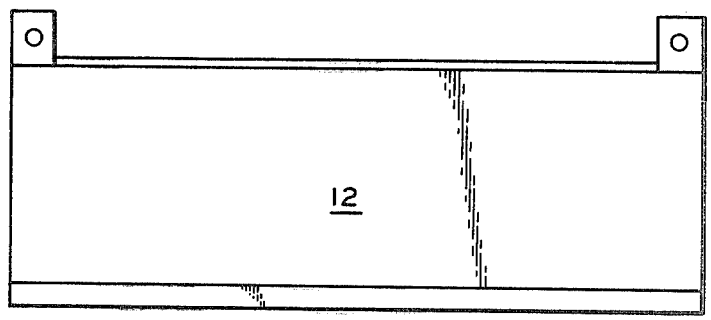
FIG._3.
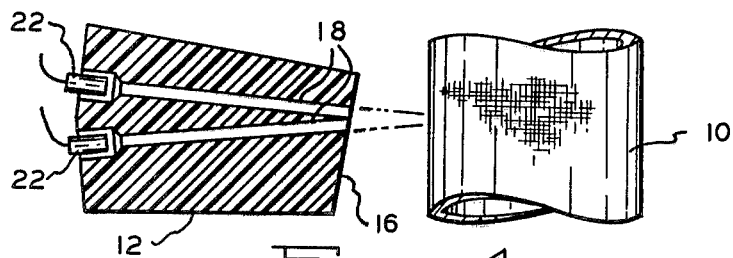
FIG._4.
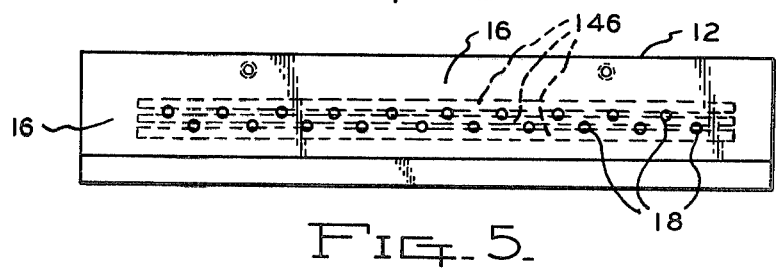
FIG._5.
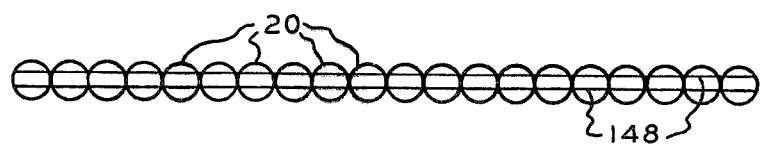
FIG._6.

DEFECT DETECTION SYSTEM

BACKGROUND OF THE INVENTION

In the machine weaving and knitting of fabric, defects occur due to missed stitches, loops and knots, apparatus malfunctioning, misalignment, or other reasons, and such defects, if occasionally occurring at random, are accepted as an economic necessity. However, frequently recurring defects such as produced by broken needles or apparatus, snags, etc., will cause a fabric machine to produce unacceptable material, and if the malfunction is not quickly remedied considerable scrap material is produced, and the likelihood of more serious damage to the knitting or weaving machine is present. Previously, most machine knitting and weaving fabric was visibly inspected, but due to the fact that one operator was responsible for a number of machines considerable material waste was produced due to breakage or malfunction.

Defect detection apparatus has been developed for fabric producing machines, and such apparatus may use light reflection techniques for scanning fabric as shown in U.S. Pat. Nos. 3,160,759; 3,589,816; 3,786,265; 4,057,351; 4,075,498 and 4,103,177. Additionally, it is known to use scanning apparatus employing light frequencies other than visible frequencies and infrared and ultraviolet band frequencies have been employed as shown in U.S. Pat. Nos. 3,206,606; 3,325,649; 3,551,678 and 3,994,586.

Inspection apparatus such as that shown in the aforementioned patents is capable of sensing defects, however, such prior art devices do not have the capability to determine when the rate of occurrence of defects is acceptable or objectionable, and such apparatus which terminates knitting or weaving machine operation upon the sensing of a single defect reduces the machine's output to unacceptable low levels. There is the need for automatic fabric inspection apparatus which is capable of analyzing the defect characteristics and determining when the rate of defect occurances is tolerable and intolerable with respect to the rate of production and the quality of product desired. Prior art devices are incapable of meeting this need.

It is an object of the invention to provide fabric defect detection apparatus capable of detecting fabric defects and producing a signal wherein the number of defects occurring may be counted and retained.

A further object of the invention is to provide fabric defect detection apparatus utilizing infrared band scanning wherein fabric defects produce an electronic signal which is retained and counted, and timing apparatus is associated with the counting and retaining apparatus whereby a control signal is produced upon a predetermined number of defects occurring within a predetermined time interval so as to permit a given quality of product to be automatically maintained.

An additional object of the invention is to provide fabric defect detection apparatus capable of simultaneously scanning a signficant portion of the fabric wherein an electronic signal is produced upon a defect being detected, the apparatus being capable of recognizing the same defect upon being repetitiously sensed, and rejecting such repetitious sensing of a common defect as a plurality of defects for machine control purposes.

A further object of the invention is to provide fabric defect detection apparatus which is electronically controlled, is capable of retaining and counting defect signals, and uitlizes timer apparatus wherein the number of defects occurring in a predetermined time frame are sensed, the timer apparatus being initiated by a defect occurring, and the timer apparatus being reset upon termination of the predetermined time interval.

In the practice of the invention a sensing head of elongated length, such as 5 inches, is located adjacent a moving fabric which has just been knitted or woven by conventional fabric producing apparatus. The fabric being sensed may be moving as a linear web, or the fabric may be in the form of a tube which is rotating. The sensing apparatus is located adjacent the newly manufactured fabric and includes an infrared light source illuminating the portion of the fabric being sensed by infrared light detecting means. The detecting means consists of a block having a plurality of light receiving openings defined therein, and a sensitive, electronic, infrared, light detector being located adjacent each light passage wherein the passing of a defect past a fabric portion reflecting light into a given passage will cause a variation in the amount of light reflected into that passage producing an electronic variation in the light receiving sensor to produce an electronic signal.

The electronic signal produced due to a defect passing the sensor is amplified, compared with a background control signal, filtered, and electronically counted. The electronic counting apparatus is also associated with an electronic timer whose time frame is initiated by the first counted defect being sensed, and as subsequent defects are signaled during an initiated time frame such defects are counted and if the number of defects occurring within the predetermined time frame is greater than a predetermined number the apparatus will be automatically stopped, and adjustments will be made by the operator to correct the problem.

The electronic timer includes means for varying the duration of the time frame during which defects are counted, and thus, it will be appreciated that the apparatus is capable of closely regulating the quality of the fabric being produced in that the number of defects acceptable within a predetermined time interval regulates the quality of the product, and should the rate of defect occurrence exceed that desired the apparatus will automatically shut down and not produce scrap material. The fact that the apparatus is capable of continually determining and evaluating the quality of the fabric being manufactured prevents excessive attention to the equipment, as is the case with fabric defect detection devices which stop the knitting or weaving machine upon a single defect occurring.

The defect detection apparatus also includes means for analyzing the defect signals it receives in that repetitive signals may mean that the sensor is repeatedly detecting the same defect, as when the advance of the fabric is less than the length of the sensing array, and the circuit of the invention would count such signals as a single defect and thereby prevent unnecessary machine shut-down.

The circuit of the defect detection system of the invention includes means for automatically sensing the reflecting characteristics of the fabric being sensed to reflect infrared light and automatic background control means are used to modify the circuit with respect to this fabric characteristic so as to achieve a uniformity of circuit operation regardless of the reflectance of the fabric being sensed.

The defect detection apparatus includes means for analyzing the defect signals it receives, in that repetitive signals may mean that the sensor is repeatedly detecting the same defect, e.g. a run, and the circuit of the invention would shut down the machine to prevent production of unacceptable material.

The defect detection system also includes signal producing means for counting the total number of defects that occur, and also is conscious of repetitive defects for terminating machine operation. Likewise, the circuit may include a large hole detector wherein a single large defect such as produced by a major machine malfunction can be quickly detected to deactivate the fabric producing machine.

BRIEF DESCRIPTION OF THE DRAWINGS

The aforementioned objects and advantages of the invention will be appreciated from the following description and accompanying drawings wherein:

FIG. 1 is a schematic, elevational view of a typical defect detection apparatus in accord with the invention, FIG. 2 is a rear elevational view of a sensing head in accord with the invention, FIG. 3 is a plan view of the sensing head, FIG. 4 is an elevational sectional view taken through Section IV—IV of FIG. 2, illustrating the infrared light receiving passages, FIG. 5 is a front elevational view of the sensing block, FIG. 6 is an illustrative view of the sensing pattern on the fabric.

DESCRIPTION OF THE PREFERRED EMBODIMENT

Figure 7:
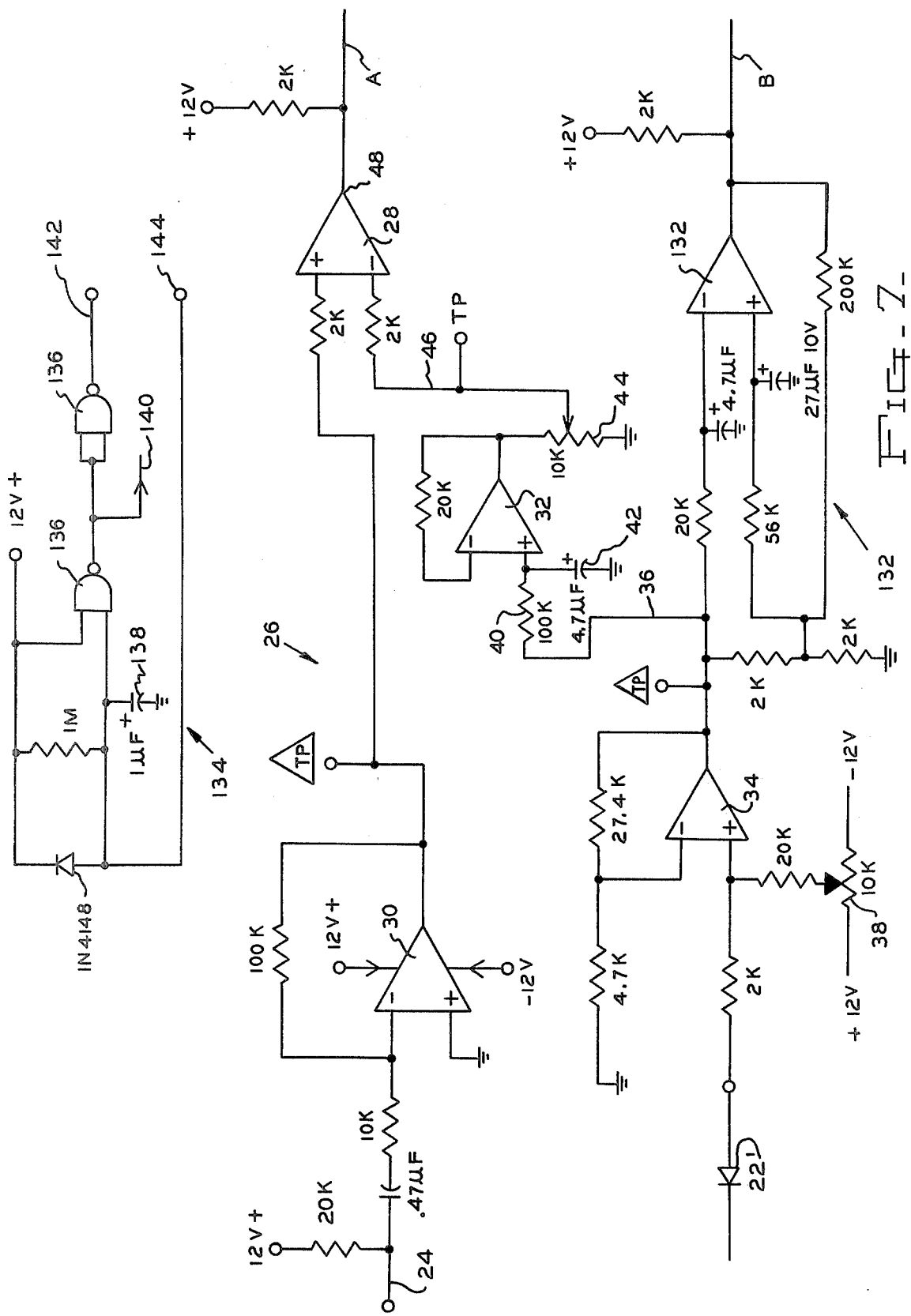
FIG. 7 is a circuit diagram partially illustrating the electronic circuit of a defect detection system in accord with the invention.

In FIG. 1 a typical installation of a fabric defect detection system in accord with the invention as used with a knitting machine is shown. The knitting machine, not shown, by means of typical knitting apparatus produces a woven fabric tube 10 which axially moves in a vertical manner and rotates about a vertical axis simultaneously moving in the directions indicated by the arrows.

The defect detection system includes a sensing head block 12 which is mounted adjacent the fabric tube 10 and the apparatus also includes a light source 14, preferably producing light within the infrared frequency band, to illuminate the portion of the fabric immediately adjacent the sensing head 12. The sensing head block is of a generally rectangular configuration having a front end face 16 disposed adjacent the fabric being inspected. The block 12 is internally provided with a plurality of light receiving passages 18, FIG. 4, each terminating at an opening at the intersection with the block face 16. Adjacent passages 18 are angularly related to each other in the manner appreciated from FIG. 4, and extention of the passages 18 beyond the face 16 results in a viewing pattern as shown in FIG. 6 consisting of a plurality of contingent circular area 20 defining a line approximately five inches in length whereby a five inch axial portion of the knitted fabric tube is being simultaneously sensed.

As the infrared light 14 is illuminating the fabric at the location being sensed by the head 12, the light being reflected from the fabric will enter the passages 18, and at the end of each passage is located an infrared detector 22 which comprises a photo transistor having uniform electrical conducting characteristics as long as the amount of light entering the detector is uniform. Upon a fabric defect passing the head, the reflected light entering at least one of the passages 18 will be momentarially affected due to the defect, and the amount of light will be either reduced or increased slightly. This variation in the amount of reflected infrared light entering a passage 19 will be immediately sensed by the associated detector 22 and produce an electronic signal. The detectors 22 are connected in parallel, and although sensors are associated with an elongated sensing head the movement of a single defect past the head will be immediately discerned and produce the electronic signal.

Figure 8:
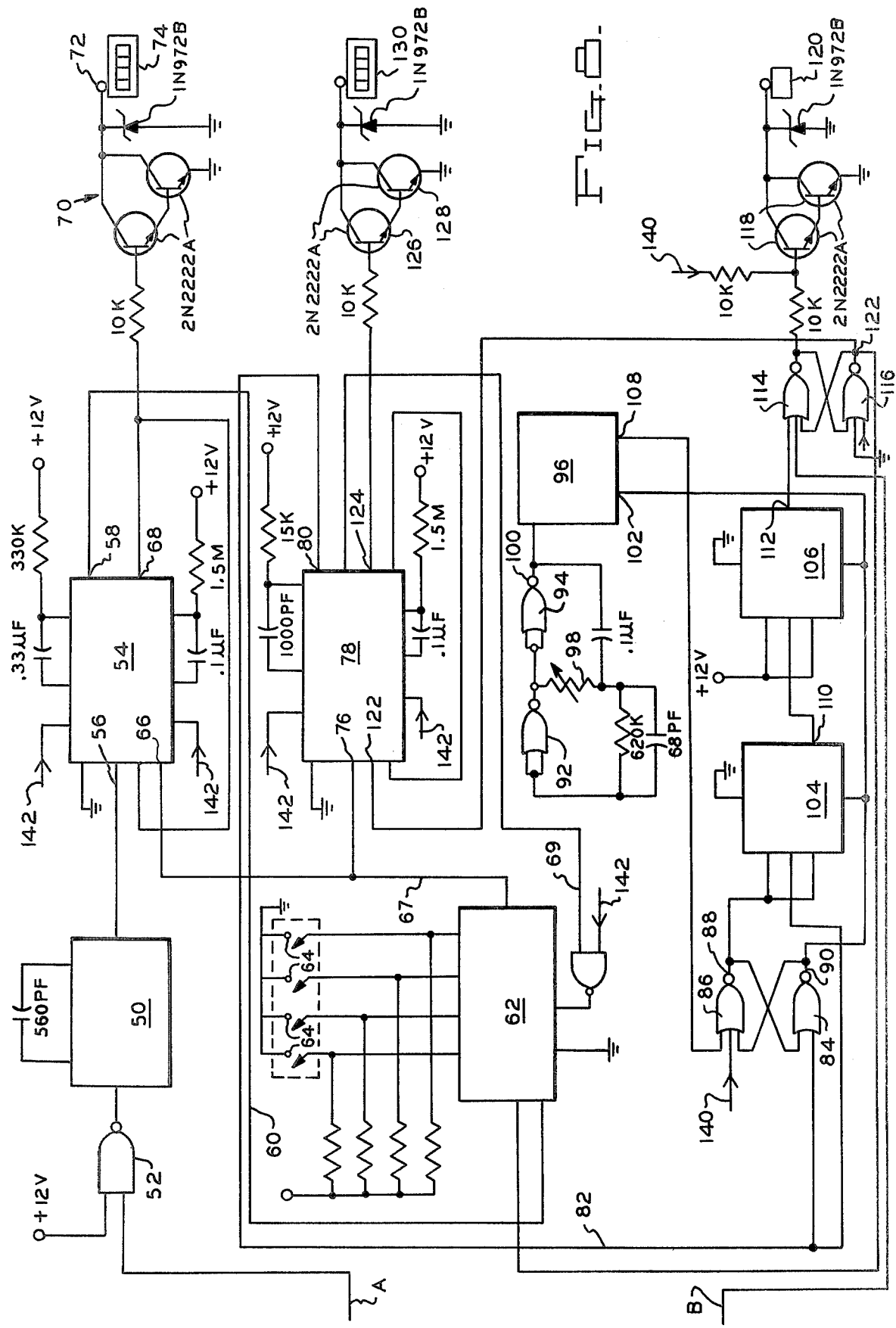
FIG. 8 is an additional figure illustrating the electronic circuit of the invention.

The circuit associated with the defect detection apparatus of the invention is illustrated in FIGS. 7 and 8, and will now be explained in detail:

The conductor 24 is attached to the output of the sensing head 12, and this signal is put into an AC coupled amplifier circuit generally indicated at 26 which produces a 20 d.b. gain. This circuit includes the voltage comparator 28, and the operational amplifier 30 and the amplified circuit produces a signal transmitted to the voltage comparator 28. The voltage comparator 28, in addition to receiving the amplified signal from the defect detection head 12, also is receiving a background threshhold voltage from the operational amplifier 32 proportional to the reflectance of the fabric. The operational amplifiers 32 and 34 constitute the automatic background control circuit, and this circuit receives its input from a phototransistor 22' receiving reflected light through a head passage 18. This phototransistor may constitute one of the phototransistors 22 utilized for defect detection, and transmits a voltage into operational amplifier 34 proportional to the amount of infrared light reflected from the fabric. This background voltage is amplified by amplifier 34 producing a DC level in conductor 36 proportional to the amount of reflected light. Potentiometer 38 is a voltage offset adjustment which compensates for the offset voltages of the operational amplifier 34, and this potentiometer permits the output to be balanced. The conductor 36 transmits a DC signal proportional to the reflected light to operational amplifier 32 and the resistor 40 and capacitor 42 smooths out the high frequency variation of the DC signal and operational amplifier 32 constitutes a unity gain buffer and potentiometer 44 permits a portion of this output threshold signal to be transmitted to the voltage comparator 28. At conductor 46 a positive threshold voltage is produced. If the signal is above the threshold voltage at conductor 46 the comparator output voltage at 48 is high, and this will indicate a fabric defect.

To filter out extraneous noise a hex debouncer 50, FIG. 8, receives the output of voltage comparator 28 through a Schmitt trigger 52 which accelerates the logic transition time to produce a definite signal. The hex debouncer 50 functions as a filter to determine if the signal is of sufficient pulse width to be interpreted as a fabric defect. The pulse input into the debouncer must be of a sufficient duration to produce a pulse output to differentiate between noise type pulses and fabric defect pulses.

The signal from debouncer 50 is transmitted to the dual monostable integrated circuit 54. The input received by integrated circuit 54 is a negative going pulse. The input at 56 is a negative trigger input such that when a pulse makes a high to low logic level transition the circuit is triggered and a pulse is produced at output 58. The output of the integrated circuit at 58 is fed by conductor 60 to a four-bit binary up-down counter 62 which counts down one pulse for every pulse that is fed into it. The counter 62 can be preset for registering a predetermined number of counts by the use of digital switches 64. Normally the counter 62 would be set for three pulses whereby this counter permits three defect signals to be produced at the sensing head before more than one defect is considered to exist. The counter 62 compensates for the fact that a single defect, as it rotates and moves in an axial direction past the head 12, may pass the head three times before its axial movement takes it beyond the sensing range of the head. The switches 64 permit the counter to be adjusted in accord with the rate of rotation of the fabric and the rate of axial advancement thereof. Counter 62 is a down counter wherein if it is set for three, three pulses will count down to zero. Upon counter 62 reaching zero terminal 66 of circuit 54 will be triggered producing a pulse output at 68, and it goes to the Darlington transistor drive stage 70 producing a pulse at 72 which is connected to a totalizer defects counter 74.

When terminal 66 is energized terminal 76 of monostable integrated circuit 78 is simultaneously energized. When the carry output of 62 is low 78 is triggered and a positive plus is produced at terminal 80 energizes conductor 82 which is connected to the two input nor gate 84 which is wired in conjunction with the triple input nor gate 86 to produce a latch circuit. The pulse sets the latch circuit and terminal 88 will go to high state and terminal 90 will go to a low state.

Under normal conditions wherein no defects have been detected, the timer circuit which includes 2 input nor gates 92 and 94 and 14-bit binary counter 96 will be inactive and not running. The timer circuit is adjustable to have a time cycle between three and twenty minutes, and this adjustment is accomplished by potentiometer 98. Gates 92 and 94 form an oscillator circuit producing a square wave output at 100. Terminal 102 of counter 96 is normally high which means that counter 96 is reset and ignores the input pulses from gate 94 because the reset overrides the clock input to counter 96.

The dual JK counters 104 and 106 constitute counting apparatus for determining the number of defects acceptable in the time frame. In the disclosed circuit three defects are permitted within the time frame, and it will be appreciated to those skilled in the art that a greater number of defects can be achieved by utilizing additional counters, or by utilizing an up-down counter similar to counter 62 employing setable switches to produce a programable counter. When the latch 84-86 is set the reset conductors on counters 96, 104 and 106 go to a low state, the counters are zeroed, and will accept the clock input, and counter 96 will begin to count up from zero. Counter 96 will count up until it reaches a count of 8192. Upon this count being reached terminal 108 will go high which resets the latch 84-86. Thus, when the timer circuit times out, the time interval will have expired and the latch 84-86 resets the timer apparatus back to its dormant stage. When the counter 96 is counting up the pulses counters 104 and 106 will accept the clock pulses so that when an additional defect is sensed counter 104 will count 1 and on the third count 106 goes to a 1. Until the first defect is sensed counters 104 and 106 are disabled, but when the first defect is sensed and counter 96 is started these counters are enabled so that 104 can accept the second defect count. Upon a third defect pulse being counted while counter 96 is in the process of counting, terminal 110 goes high and in 106 the output terminal 112 goes high which means that three defects have been counted. A latch formed by a pair of triple input nor gates 114 and 116 is set. The transistor pair 118 is turned off which actuates a relay 120 to shut the fabric producing machine off. The output at 122 goes high which produces a positive trigger at 112 at 78 and this produces a pulse at 124. The pulse at 124 goes to transistors 126 and 128 to produce a repetitive defect count at counter 130.

The circuit may include a large hole detector generally indicated at 132, this function being optional to the circuit. The large hole detector receives a signal from the automatic background control circuit which is, of course, proportional to the amount of reflected light. This circuit employs the voltage comparator 132. This circuit measures the duration of a sudden drop in the light level, and this low level, if occurring for a predetermined duration will actuate the nor gate latch 114-122 to stop the fabric apparatus producing.

A power-on reset circuit is generally indicated at 134 in FIG. 7 and is used to eliminate extraneous defect counts. Two input Nand Schmitt triggers 136 are utilized in conjunction with capacitor 138 which is normally discharged at power on and conductor 140 is high and conductor 142 is low which resets the circuit. As the power comes up, the voltage in capacitor 138 slowly charges and when the voltage reaches the threshold voltage of the Nand gate input then the output goes to a low state, 140 goes low and 142 goes high and this means that the resets are removed. The reset switch input 144 is a manual switch which is wired across the capacitor 138 to short the ground to reset the circuit. The capacitor recharges to produce the same condition as a power-on when the switch is released.

In order to provide optimum sensing accuracy of defects in the textile the openings of the passages 18 as defined with the intersection of the face 16 may be partially masked to restrict the "viewing" area of the head 12. Such masking can be accomplished by affixing opaque adhesive strips 146 to the face 16 as shown in dotted lines in FIG. 5 wherein the edges of the strips partially cover portions of the passage openings with the result that the head 12 senses a narrow "slot" on the fabric as represented by the lines 148, FIG. 6, the viewing slot being defined by the area between the lines 148. Thus, the viewing slot is of a continuous configuration, and even very small fabric defects will affect the reflection of the fabric and produce a defect signal.

Figure 9:
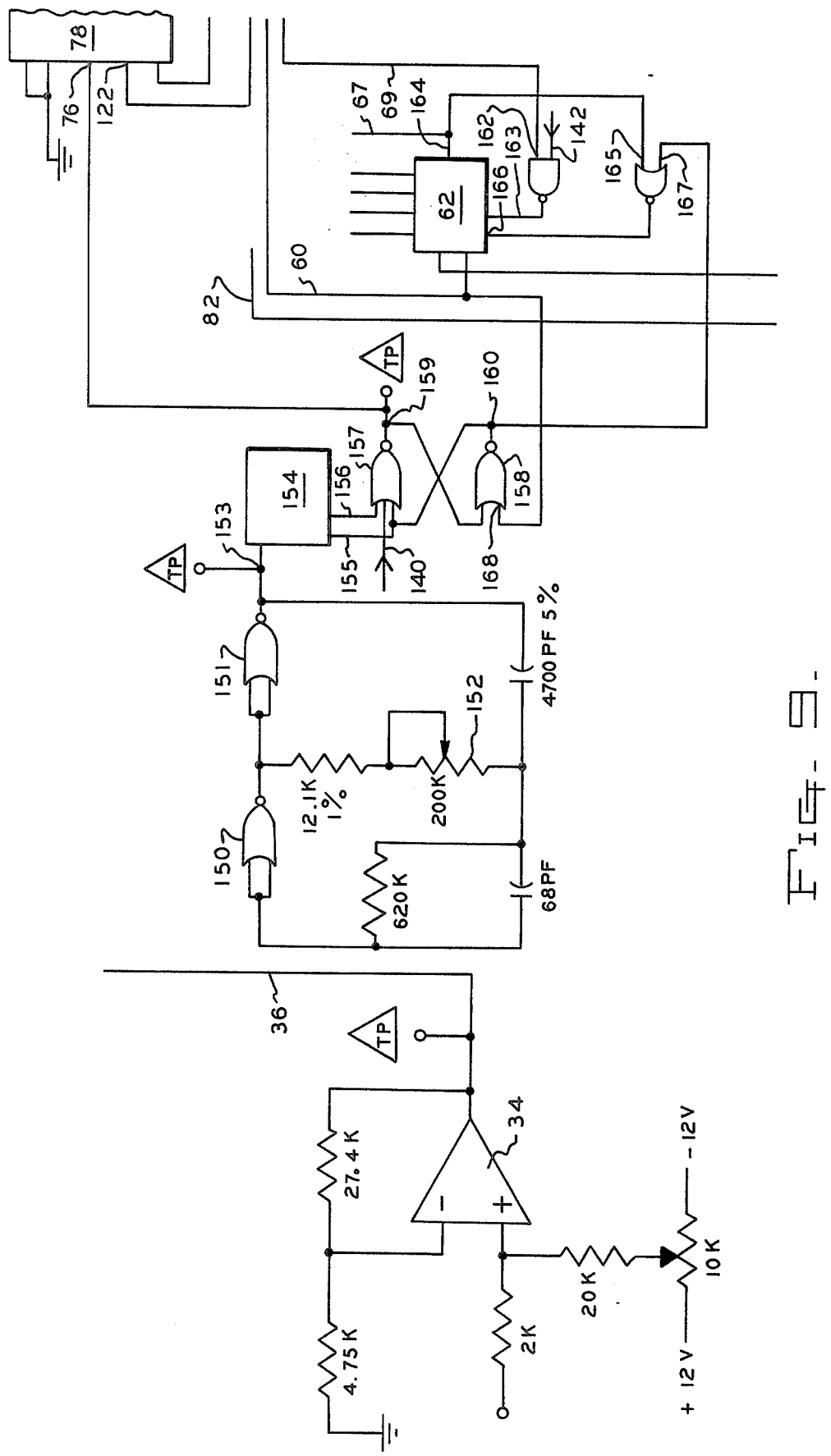
FIG. 9 is a partial circuit diagram illustrating a circuit modification.

FIG. 9 illustrates a modification in the circuit which automatically permits the counter 62 to reset in order to insure that a defect signal actually represents a defect and is counted as one defect. The circuit modification shown in FIG. 9 utilizes identical reference numerals to those previously used for the same components, and in the utilization of this modification the large hole detector circuit 132 is eliminated. Thus, the background control amplifier 34 does not have a circuit directly controlling the machine termination control relay 120, as is the case with the above described circuit. The modified circuit is described below:

The output of the integrated circuit 54 at 58 is fed via conductor 60 to the input of a 2-input nor gate 158, which forms a latch circuit with gate 157. Gates 157, 158, together with gates 150, 151 and counter 154, form a timer circuit, the function of which is to time-out the time interval during which counter 62 will accept additional input pulses. A pulse on conductor 60 sets the latch circuit 157-158 (Output 159 goes to a high logic level and output 160 goes to a low logic level). When output 160 goes low, it removes the reset at 155 from counter 154. This allows counter 154 to accept input pulses at 153 from the square wave oscillator circuit which consists of gates 150, 151 and associated circuitry. Counter 154 is a 14-bit binary counter which will count the pulses at 153 until it reaches a count of 8,192. Upon this count being reached, terminal 156 will go high, which resets latch 157-158. Counter 154 is then reset again (160 and 155 go high), and terminal 159 goes low. When terminal 159 goes low, input 76 of monostable integrated circuit 78 also goes low which triggers 78 producing a negative-going pulse at 161 and at the input of nand gate 162. This produces a positive pulse at 163 which presets counter 62, returning counter 62 to its initial state.

Also, when counter 62 reaches zero, the input of a two-input norgate at 165 goes to a low logic level. The other input of this gate at 167 is connected to the 157-158 latch circuit at 160. When the timer is running, terminal 160 is low. Thus, the output of the nor gate at 166 will be high only when the timer circuit is running and counter 62 is in the zero state. Since 166 is connected to the reset input of counter 62, a high level on this line will reset the counter and hold it in this state, effectively disabling it, until the timer latch 157-158 is reset, i.e., the timing interval passes. This feature prevents counter 62 from accumulating additional pulse counts after the preset number set by switches 64 has been counted during the predetermined time interval. This allows the defect to clear the sensing range of the head without causing additional defect counts or a residual count to remain in the counter 62. Note that if the preset number of pulse counts set by switches 64 is not reached in the predetermined time interval, which is set by the oscillator circuit 150-151 and potentiometer 152, then counter 62 will be preset and returned to its initial state. This feature also prevents a residual count from remaining in counter 62, due to random noise pulses which may be picked up by the circuit or sensing head.

From the above description it will be appreciated that the defect detection system of the invention automatically compensates for the reflectance of the fabric being inspected, filters out signals received from the sensing head to minimize the likelihood of false readings, and permits repetitive defect signals to be analyzed wherein a plurality of signals can be recognized as constituting a single defect in an apparatus wherein the fabric movement will cause the defect to be translated past the sensing head several times. The sensing of a defect initiates an adjustable timing circuit which, within the desired time frame, will not stop the fabric producing machine until a predetermined number of bonafide defects occur within the desired time frame. Thus, the quality of the fabric product can be accurately regulated and the highest acceptable production achieved. The invention permits a predetermined number of defects to exist within a given yardage of material, and as missed stitches in knitting machines occasionally occur due to no equipment malfunction or breakage fabric manufacturing apparatus utilizing the system of the invention will not be needlessly shut down and high production rates can be automatically maintained, and yet high quality products assured.

The integrated circuits illustrated are commercially available, and in the following schedule the components are identified by reference numeral, manufacturer and part number.

| Reference | Manufacturer | Part No. |
|---|---|---|
| 86, 114, 111, 157 | RCA | CD4025B |
| 28, 132 | National Semiconductor | LM339 |
| 30, 32 34 | National Semiconductor | LM324 |
| 104, 106 | RCA | CD4027B |
| 62 | RCA | CD4516B |
| 92, 94, 84 | RCA | CD4001B |
| 150, 151, 158 | RCA | CD4001B |
| 136, 52 | RCA | CD4093B |
| 154 | RCA | CD4020B |
| 78 | RCA | CD4098B |
| 96 | RCA | CD4020B |
| 50 | Motorola | MC14490 |
| 54 | RCA | CD4098B |

The reference TP indicates test points.

It is appreciated that various modifications to the inventive concepts may be apparent to those skilled in the art without departing from the spirit and scope of the invention.

We claim:

1. A defect detection system for inspecting tubular fabric wherein the fabric tube rotates about its longitudinal axis and is substantially axially translated during inspection wherein relative movement occurs between the fabric tube and fixed defect detection apparatus, comprising, in combination, electronic sensing means sensing a fabric portion having an axial length greater than the fabric axial translation during each revolution for detecting a defect in the fabric and having an electrical output producing a signal upon a defect being sensed, electronic signal counting apparatus connected to said output receiving and counting signals from said sensing means, timing apparatus associated with said signal counting apparatus whereby the number of signals produced within a predetermined interval of time can be determined, control apparatus connected to said signal counting and timing apparatus producing a control output signal upon a predetermined number of defect signals occurring while a predetermined time interval and defect indentification means incorporated into said signal counting apparatus, said defect identification means recognizing repetitive defect signals within a given time interval to produce a single signal for defect determination purposes.

2. In a defect detection system as in claim 1, adjustable means associated with said defect identification means for varying the number of defect signals necessary to produce a defect control signal.

3. In a defect detection system as in claim 1, said defect identification means including timing means for automatically resetting said signal counting apparatus if repetitive defect signals do not occur within a predetermined time interval.

4. In a defect detection system as in claim 1, said electronic counting apparatus initiating said timer apparatus whereby said timer apparatus predetermined time interval is initiated upon a defect being sensed.

5. In a defect detection system as in claim 4, reset means incorporated into said timer apparatus resetting said timer apparatus upon expiration of said predetermined time interval.

6. In a defect detection system as in claim 1, an infrared light source illuminating the fabric portion being sensed, said electronic sensing means comprising infrared sensitive detectors receiving reflected infrared frequencies from the fabric being sensed, infrared frequency intensity sensing means producing a background control voltage proportional to the ability of the fabric being sensed to reflect infrared frequencies, and voltage comparator means comparing said sensing means output defect signal with said background control voltage to permit consistent operation of said sensing means.

7. In a defect detection system as in claim 1 wherein said signal counting apparatus comprises first and second counters, said first counter comprising said defect identification means and said second counter counts the total number of defects sensed within said predetermined interval of time.

* * * * *